(12) United States Patent
Shi et al.

(10) Patent No.: US 10,285,994 B2
(45) Date of Patent: May 14, 2019

(54) METHOD OF PREVENTING OR TREATING OSTEOPOROSIS BY NEDDYLATION INHIBITOR

(71) Applicants: Chang Gung University, Tao-Yuan (TW); Chiayi Chang Gung Memorial Hospital, Chiayi County (TW)

(72) Inventors: Chung-Sheng Shi, Tainan (TW); Meng-Huang Wu, Taipei (TW); Kuo-Ti Peng, Hsinchu County (TW)

(73) Assignees: CHANG GUNG UNIVERSITY, Tao-Yuan (TW); CHIAYI CHANG GUNG MEMORIAL HOSPITAL, Chiayi County (TW)

( * ) Notice: Subject to any disclaimer, the term of this patent is extended or adjusted under 35 U.S.C. 154(b) by 0 days.

(21) Appl. No.: 15/957,951

(22) Filed: Apr. 20, 2018

(65) Prior Publication Data

US 2018/0303833 A1    Oct. 25, 2018

(30) Foreign Application Priority Data

Apr. 21, 2017 (TW) .............................. 106113484 A

(51) Int. Cl.

| | | |
|---|---|---|
| *A61K 48/00* | (2006.01) |
| *C07H 21/02* | (2006.01) |
| *C07H 21/04* | (2006.01) |
| *A61K 31/519* | (2006.01) |
| *A61K 31/12* | (2006.01) |
| *A61K 31/352* | (2006.01) |
| *A61K 31/555* | (2006.01) |
| *A61K 31/7088* | (2006.01) |
| *C12N 15/113* | (2010.01) |
| *A61P 19/10* | (2006.01) |

(52) U.S. Cl.
CPC ............ *A61K 31/519* (2013.01); *A61K 31/12* (2013.01); *A61K 31/352* (2013.01); *A61K 31/555* (2013.01); *A61K 31/7088* (2013.01); *A61P 19/10* (2018.01); *C12N 15/1137* (2013.01); *C12N 2310/14* (2013.01)

(58) Field of Classification Search
CPC . A61K 31/713; A61K 2300/00; C12N 15/111
See application file for complete search history.

(56) References Cited

U.S. PATENT DOCUMENTS 9,447,156 B2 * 9/2016 Monda ...................... C12N 9/93
2016/0339019 A1 * 11/2016 Laberge ............... A61K 31/428

* cited by examiner

*Primary Examiner* — Amy H Bowman

(57) ABSTRACT

Disclosed herein is a method of preventing and/or treating abnormal bone resorption and/or osteoporosis in a subject in need thereof. The method comprises administering to the subject an effective amount of an inhibitor on inhibiting neddylation. According to some embodiments of the present disclosure, the inhibitor on inhibiting neddylation is a NAE inhibitor, which includes but is not limited to, MLN4924.

9 Claims, 15 Drawing Sheets
(5 of 15 Drawing Sheet(s) Filed in Color)
Specification includes a Sequence Listing.

METHOD OF PREVENTING OR TREATING
OSTEOPOROSIS BY NEDDYLATION
INHIBITOR

CROSS-REFERENCE TO RELATED APPLICATIONS

This application relates to and claims the benefit of TW Non-provisional Application No. 106113484, filed Apr. 21, 2017; the content of the application is incorporated herein by reference in its entirety.

BACKGROUND OF THE INVENTION

1. Field of the Invention

The present disclosure in general relates to the field of osteoporosis treatment. More particularly, the present disclosure relates to a method of treating osteoporosis by use of a neddylation inhibitor.

2. Description of Related Art

Osteoporosis is a disorder characterized by low bone density, which is an important risk factor for bone fracture in older adults. Osteoporosis is more common in women than men. In developed countries, approximately 2-8% males and 9-38% females are diagnosed with osteoporosis. Osteoporosis does not in itself cause any symptom to the subject, except an increased risk of bone fractures. Osteoporotic fractures usually occur in situations where healthy people would not normally break a bone. Typical osteoporotic fractures include hip, vertebral, wrist and rib fractures.

The differentiation and activation of osteoclasts from the monocyte/macrophage hematopoietic lineage is majorly mediated by receptor activator of nuclear factor kappa-B ligand (RANKL) signaling on normal bone matrix remodeling. The over-activation of osteoclasts secretes acid and lytic enzymes that degrade bone matrix can result in osteolytic bone diseases and osteoporosis. Therefore, targeting the differentiation and functional activity of osteoclasts have afforded insights into the means of osteoclastogenesis and activation of bone resorption for developing the potential therapies on treating osteoporosis and other diseases of bone loss.

It has been reported that bone loss increases after menopause due to lower levels of estrogen. In addition, several factors also contribute to the development of osteoporosis, including alcoholism, caffeine, tobacco smoking, vitamin D deficiency, malnutrition, heavy metal (e.g., cadmium and lead), hyperthyroidism, kidney disease, and medication (e.g., aromatase inhibitors, methotrexate, proton pump inhibitor, and steroid etc.).

Smoking cessation, moderate intake of alcohol intake and specific supplements (such as calcium and vitamin D) are reported to be useful in the prevention of osteoporosis. As to the medications, bisphosphonate (a class of drugs for preventing the loss of bone mass), estrogen (also known as oestrogen, the primary female sex hormone associated with bone deposition), Teriparatide (a recombinant parathyroid hormone with effect on stimulating the formation of new bone and restoring lost bone mass), Raloxifene (an estrogen receptor modulator having effect on reducing the level of bone metabolism), Denosumab (a monoclonal antibody inhibitor of receptor activator of nuclear factor κ-B ligand (RANKL) on suppressing the development of osteoclasts), Calcitonin (a calcium regulatory hormone, strongly inhibiting bone-resorbing activity of osteoclast), and strontium ranelate (a strontium(II) salt of ranelic acid, stimulating the formation of new bone tissue and decreasing bone resorption) provide potential means to treat osteoporosis and/or osteolytic diseases. However, each of therapeutic approaches listed above has its limitation. For example, bisphosphonate usually causes abdominal pain, nausea, vomiting, dyspepsia, musculoskeletal pain and osteonecrosis of the jaw. Estrogen may increase the risk of heart attack, blood-clot formation, stroke, endometrial hyperplasia and breast and endometrial cancers. The most common adverse effects associated with teriparatide include injection-site pain, nausea, headaches, leg cramps and dizziness. Raloxifene may increase the risk of blood-clot formation and stroke. Denosumab may result in hypocalcemia and steonecrosis of the jaw; further, it also compromises the immune response to microorganism infection. Calcitonin is associated with allergy and the development of difference cancers. Regarding strontium ranelate, it may cause nausea, diarrhea, headache, seizures, memory loss and consciousness disturbances.

In view of the foregoing, there exists in the related art a need for a novel method of safely and effectively preventing and/or treating abnormal bone resorption and/or osteoporosis so as to improve the life quality and life span of the subject in need thereof.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is directed to a method of preventing and/or treating osteoporosis in a subject in need thereof. The method comprises administering to the subject an effective amount of a neddylation inhibitor.

According to some embodiments of the present disclosure, the neddylation inhibitor is an NEDD8-activating enzyme (NAE) inhibitor. According to preferred embodiments, the NAE inhibitor may be a compound or a synthetic nucleic acid. Non-limiting examples of the NAE inhibitor include, MLN4924 and the analog and derivative thereof, TAS4464, 6,6"-biapigenin, cyclometallated rhodium (III) complex [Rh(ppy)$_2$(dppz)]$^+$, and flavokawain A. According to one specific working example, the NAE inhibitor is MLN4924. According to another example of the present disclosure, the NAE inhibitor is the synthetic nucleic acid, which comprises the sequence of SEQ ID NO: 4 or 6, or a DNA sequence corresponding thereto; in this example, the synthetic nucleic acid is useful in down-regulating the expression of UBA3, the catalytic subunit of NAE.

The synthetic nucleic acid may be a small interference ribonucleic acid (siRNA), a small hairpin ribonucleic acid (shRNA), or a micro-ribonucleic acids (miRNA). According to one working example of the present disclosure, the synthetic nucleic acid is the siRNA.

According to certain embodiments of the present disclosure, the subject may be a mouse, in which the neddylation inhibitor is administered in the amount of 0.125-1,250 mg/kg body weigh per day; preferably, 1.25-125 mg/kg body weigh per day; more preferably, 1.25-25 mg/kg body weigh per day. According to one specific example, the neddylation inhibitor is administered to the subject in the amount of 10 mg/kg body weigh per day.

In the case when the subject is a human, the human equivalent dose (HED) of the neddylation inhibitor to be administered onto the human subject may be calculated based on the doses determined from animal studies. Accordingly, the effective amount of the neddylation inhibitor for use on a human subject is about 0.01-100 mg/kg body weigh per day; preferably, about 0.1-10 mg/kg body weigh per day; more preferably, about 0.1-2 mg/kg body weigh per day.

According to some embodiments of the present disclosure, the neddylation inhibitor is administered to the subject daily for at least 7 consecutive days; preferably, for at least 14 consecutive days, so as to suppress the development of osteoporosis.

The present neddylation inhibitor may be administered by a route selected from the group consisting of oral, enteral, nasal, topical, transmucosal, and parenteral administration, in which the parenteral administration is any of subcutaneous, intradermal, intramuscular, intraarterial, intravenous, intraspinal, intrathecal or intraperitoneal injection.

Also disclosed herein is a synthetic nucleic acid comprising the sequence of SEQ ID NO: 4 or 6, or a DNA sequence corresponding thereto, in which the synthetic nucleic acid down-regulates the expression of UBA3, the catalytic subunit of NAE. The synthetic nucleic acid may be a siRNA, a shRNA, or a miRNA.

Optionally, the 5'-end and/or 3'-end of the synthetic nucleic acid is modified with a fluoro, methoxy, or methoxyethyl group.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where:

FIG. 1A: the photographs of TRAP staining depicting the differentiation of osteoclasts from BMMs. FIG. 1B: after the differentiation of osteoclasts in Corning Osteo Surface (a synthetic 3-dimensional structure that mimics in vivo bone for in vitro bone cell assays), the cells were removed, and the resorbed areas for confirming osteoclast activity were analyzed by 1% toluidine blue staining. FIG. 1C: the culture medium is subject to Biovision Cathepsin K Activity Fluorometric Assay Kit for the analysis of cathepsin K activity. FIG. 1D: the effect of effective doses of MLN4924 on the viability of BMMs is evaluated by MTT assay. Scale bar represents 100 μm. Data are expressed as mean±SD where *$p<0.05$; **$p<0.01$.

FIG. 2A: the photographs of TRAP staining depicting the differentiation of osteoclasts from RAW264.7 cells. FIG. 2B: after the differentiation of osteoclasts in Corning Osteo Surface, the cells were removed, and the resorbed areas for confirming osteoclast activity were analyzed by 1% toluidine blue staining. FIG. 2C: the culture medium is subject to Biovision Cathepsin K Activity Fluorometric Assay Kit for the analysis of cathepsin K activity. FIG. 2D: the effect of effective doses of MLN4924 on the viability of RAW264.7 cells is evaluated by MTT assay. Scale bar represents 100 μm. Data are expressed as mean±SD where *$p<0.05$.

FIG. 3A: the time course effect of MLN4924 on the phosphorylations of ERK (pERK), P38 (pP38) and JNK (pJNK). FIG. 3B: the dose effect of MLN4924 on the phosphorylations of ERK (pERK), P38 (pP38) and JNK (pJNK). FIG. 3C: the time course effect of MLN4924 on the expression of NFATc-1. FIG. 3D: the dose effect of MLN4924 on the expression of NFATc-1. Mock: untreated control; R: sRANKL; M: MLN4924.

FIG. 4A: the growth of MC3T3-E1 cells during osteogenesis is analyzed by crystal violet staining. FIG. 4B: the osteogenesis of MC3T3-E1 cells on day 21 is analyzed by measuring Alizarin Red S stain. Diff: osteoblast differentiation medium. MLN: MLN4924.

FIG. 5A: RAW264.7 mouse macrophages were seeded on wells and were treated with various concentrations of sRANKL (0-100 ng/ml). After 72 hours' incubation, the cells were lysed and subjected to Western blotting analysis using specific antibodies in neddylation pathway. FIG. 5B: RAW264.7 mouse macrophages were seeded on wells and transfected with UBA3 or scrambled siRNA. After culture, the transfected cells were harvested, lysed, and further analyzed by Western Blot for checking NEDD8, UBA3, and APPBP1 expressions. FIGS. 5C and 5D: the UBA3 or scrambled siRNA transfected RAW264.7 cells were further treated with sRANKL (50 ng/ml), after 3-day induction, the morphological change of macrophages to TRAP-stained positive giant osteoclasts were photographed and further counted. Data are expressed as mean±SD where *$p<0.05$.

FIG. 6A: Micro computed-tomography (micro-CT) three-dimensional images of the distal femurs of mice respectively treated with the indicated treatments, in which the left panels represent transaxial plane, and the right panels represent coronal plane. FIGS. 6B-6D: micro-CT measurement of trabecular bone parameters, including bone volume/total volume (FIG. 6B), trabecular number (FIG. 6C), and trabecular space (FIG. 6D). FIG. 6E: Serum level of C-telopeptide of type 1 collagen (CTX-1) in control, OVX, OVX+sRANKL, and OVX+sRANKL+MLN4924 groups. Values are expressed as mean±SD, N=6 per group. *$p<0.05$; **$p<0.01$.

DETAILED DESCRIPTION OF THE INVENTION

Figure 1A:
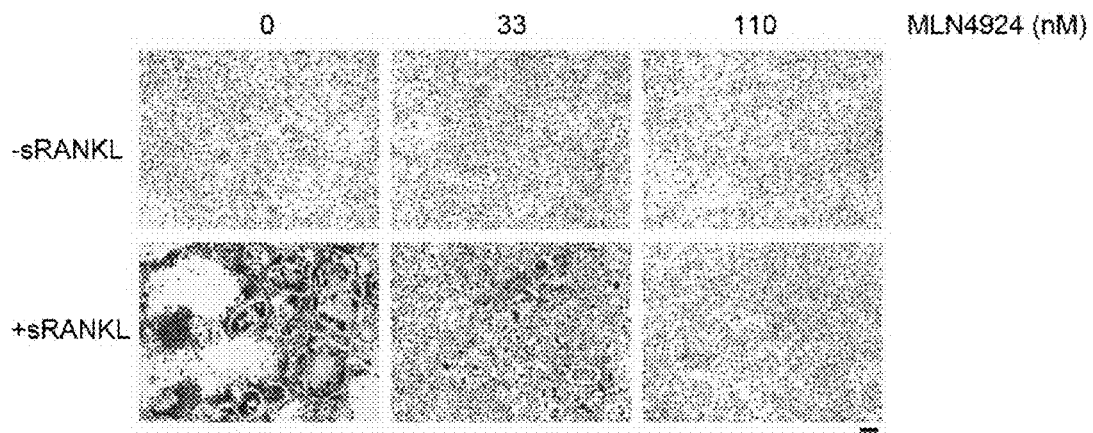
FIGS. 1A-1D are data collected from primary mouse bone marrow-derived macrophages (BMMs) respectively incubated in the medium containing the soluble recombinant RANKL (sRANKL, 50 ng/ml), macrophage colony-stimulating factor (M-CSF, 40 ng/ml) and specified concentrations of MLN4924 for 7 days according to example 1.1 of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Unless specified otherwise, in the polynucleotide notation used herein, the left-hand end is the 5'-end and the right-hand end is the 3'-end, in accordance with standard usage.

As used herein, the term "analogs of MLN4924" refers to those compounds, enantiomers, and derivatives of MLN4924, which are derived from MLN4924 and retain all or part of the biological function of MLN4924.

The term "derivatives of MLN4924" refers to those compounds, enantiomers and analogs of MLN4924, which are derived from MLN4924 and retain all or part of the biological function of MLN4924.

The terms "application" and "administration" are used interchangeably herein, and are intended to mean administering to a subject (e.g., a subject who is at risk of developing abnormal bone resorption and/or osteoporosis, or a subject having or suspected of having abnormal bone resorption and/or osteoporosis) the present neddylation inhibitor (e.g., MLN4924) thereby decreasing the risk of developing abnormal bone resorption and osteoporosis, or alleviating or ameliorating the symptoms associated with osteoporosis or RANKL-mediated abnormal bone resorption. According to various embodiments of the present disclosure, the present neddylation inhibitor may be administered to the subject via an appropriate route (e.g., intravenous injection, intraperitoneal injection, or oral administration) so as to prevent and/or treat osteoporosis and/or bone mass loss.

As used herein, the term "treat" or "treatment" refers to the application or administration of the present neddylation inhibitor (e.g., MLN4924) to a subject, who has osteoporosis and/or abnormal bone resorption, a symptom of osteoporosis and/or abnormal bone resorption, or a predisposition toward osteoporosis and/or abnormal bone resorption, with the purpose to prevent, cure, heal, alleviate, relieve, alter, remedy, ameliorate, improve, or affect osteoporosis and/or abnormal bone resorption, the symptom of osteoporosis and/or abnormal bone resorption, or the predisposition toward osteoporosis and/or abnormal bone resorption. Non-limiting examples of the symptom associated with osteoporosis and/or abnormal bone resorption include, fracture (such as hip fracture, vertebral fracture, wrist fracture and rib fracture), back pain, kyphosis (curved back) and osteolytic diseases.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the present neddylation inhibitor), such as molar concentration, mass concentration, volume concentration, molality, mole fraction, mass fraction and mixing ratio. Specifically, the term "therapeutically effective amount" used in connection with the neddylation inhibitor described herein refers to the quantity of neddylation inhibitor, which is sufficient to alleviate or ameliorate the symptoms associated with the osteoporosis and/or abnormal bone resorption in the subject. Persons having ordinary skills could calculate the human equivalent dose (HED) for the medicament (such as the present neddylation inhibitor) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to a mammal including the human species that is treatable with methods of the present invention. The term "subject" is intended to refer to both the male and female gender unless one gender is specifically indicated. According to preferred embodiments of the present disclosure, the subject may be human, mouse, rat, guinea pig, hamster, monkey, swine, dog, cat, horse, sheep, goat, cow or rabbit.

The present disclosure is based, at least in part, on the discovery that the neddylation inhibitor can suppress the differentiation and/or function of osteoclasts thereby preventing or diminishing abnormal bone resorption and bone mass loss. Accordingly, the first aspect of the present disclosure pertains to a method of preventing and/or treating osteoporosis and/or abnormal bone resorption in a subject.

According to embodiments of the present disclosure, the method comprises administering to the subject an effective amount of a neddylation inhibitor. In general, the neddylation inhibitor may be any antagonist that inhibits the neddylation pathway, for example, an antagonist peptide or an antagonist compound of neddylation pathway. According to certain embodiments of the present disclosure, the neddylation inhibitor may specifically inhibit the activity of NAE. The NAE inhibitor may be a compound or a synthetic nucleic acid. Exemplary compounds suitable for use in the present method include, but are not limited to, MLN4924 and the analog and derivative thereof, TAS4464, 6,6"-biapigenin, cyclometallated rhodium (III) complex (e.g., [Rh(ppy)$_2$(dppz)]$^+$), and flavokawain A.

According to preferred embodiments of the present disclosure, the neddylation inhibitor is MLN4924, or an analog or a derivative thereof, in which MLN4924 is a short name for (1S,2S,4R)-4-(4-(((1S)-2,3-Dihydro-1H-inden-1-ylamino)-7H-pyrrolo(2,3-d)pyrimidin-7-yl)-2-hydroxycyclopentyl) methyl sulphamate.

Regarding the synthetic nucleic acid, it may be a siRNA, a shRNA, or a miRNA, which targets the catalytic subunit UBA3 of NAE. According to some embodiments of the present disclosure, the synthetic nucleic acid is the siRNA. In the preferred embodiments, the siRNA has a sense strand (serving as the passenger strand) and an anti-sense strand (serving as the guide strand to silence the gene expression), in which the sense strand has the nucleotide sequence of SEQ ID NO: 3, and the anti-sense strand has the sequence of SEQ ID NO: 4. According to an alternative example, the sense strand of the siRNA has the nucleotide sequence of SEQ ID NO: 5, and the anti-sense strand of the siRNA has the nucleotide sequence of SEQ ID NO: 6.

As could be appreciated by persons having ordinary skill in the art, the silencing or inhibition of mRNA translation can be achieved by nucleotide molecules other than siRNAs, and these nucleotide molecules are also contemplated by embodiments of the present invention. For instance, shRNA is an RNA molecule that contains sense and anti-sense sequences connected by a short spacer of nucleotides that enables the molecule to form a loop structure, and according to embodiments of the present disclosure, the synthetic nucleic acid can be shRNA, in which the sense sequence of the shRNA is identical to the sequence of SEQ ID NO: 3 or 5, and the anti-sense sequence of shRNA is identical to the sequence of SEQ ID NO: 4 or 6. Alternatively, the synthetic nucleic acid is provided in the form of an miRNA or a precursor (e.g., pri-miRNA or pre-miRNA) thereof, and the miRNA or the precursor has a sequence comprising the sequences of SEQ ID NO: 4 or 6. Still alternatively, the synthetic nucleic acid can be any double- or single-stranded antisense oligonucleotide comprising the sequence of SEQ ID NO: 4 or 6, or the DNA sequence corresponding thereto (i.e., the DNA sequence corresponding to the RNA sequence of SEQ ID NO: 4 or 6).

The synthetic nucleic acid may have various modifications that protect the stability of the synthetic nucleic acid, prolong the lifetime of the synthetic nucleic acid, potentiate the function of the synthetic nucleic acid, or target the synthetic nucleic acid to specific tissues/cells. For example, the 5'-end and/or 3'-end of the synthetic nucleic acid may be modified with a fluoro (—F), methoxy (—OCH$_3$; O-Me), or methoxyethyl (—OCH$_2$CH$_2$OCH$_3$; O-MOE) group. Specifically, for the purpose of increasing the stability of synthetic nucleic acid, the ribose 2'-OH group of the synthetic nucleic acid may be substituted with 2'-O-methyl (2'-O-Me), 2'-fluoro (2'-F) and 2'-methoxyethyl (2'-O-MOE). Additionally or alternatively, the 5'-end or the 3'-end of the synthetic nucleic acid may be modified with a cholesterol or thiol group thereby increasing the efficacy of the synthetic nucleic acid on delivery and cell penetration. As could be appreciated, the 5'-end or the 3'-end of the synthetic nucleic acid may be conjugated with a molecule, for example a fluorescent molecule.

According to one embodiment, the subject treatable by the present method is at risk of developing osteopenia, osteoporosis, and/or abnormal bone resorption. According to another embodiment, the subject treatable by the present method has or is suspected of having osteoporosis and/or abnormal bone resorption. According to still another embodiment, the subject treatable with the present method has or is suspected of having osteopenia.

According to some embodiments of the present disclosure, the subject is a mouse. In these embodiments, the neddylation inhibitor is administered to the subject in an amount of 0.125-1,250 mg/kg body weigh per day; preferably, 1.25-125 mg/kg body weigh per day; more preferably, 1.25-25 mg/kg body weigh per day. According to one specific example, the neddylation inhibitor is administered in an amount of 10 mg/kg body weigh per day.

A skilled artisan may readily determine the human equivalent dose (HED) of the present neddylation inhibitor, based on the doses determined from animal studies provided in working examples of this application. According to some embodiments the amount of the present neddylation inhibitor suitable for use in a human subject may be in the range of about 0.01-100 mg/Kg/day, such as 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/kg body weight per day for human; preferably, 0.1-10 mg/kg body weigh per day; more preferably, 0.1-2 mg/kg body weigh per day.

As would be appreciated, the dosing regimen may vary with specified factors, such as age, gender, bone mass, physiological condition, and other treatments (if any). For example, the present neddylation inhibitor may be administered to the subject 1-7 times per week (e.g., 1, 2, 3, 4, 5, 6 or 7 times per week) for 1, 2, 3, 4 or more consecutive weeks. Alternatively, the neddylation inhibitor may be administered to the subject 1-10 times (e.g., 1, 2, 3, 4, 5, 6, 7, 8, 9 or 10 times) for every 2 weeks, every 4 weeks, every 5 weeks, every 6 weeks, every 7 weeks, every 8 weeks, every 9 weeks, or every 10 weeks; or once every month, every 2 months, or every 3 months, or longer. According to one working example of the present disclosure, the neddylation inhibitor is administered to the subject daily for at least 2 weeks (for 2, 3 or 4 consecutive weeks) so as to produce the preventive/therapeutic effect.

According to one embodiment of the present disclosure, the neddylation inhibitor may suppress the differentiation and/or function of osteoclasts via modulating the RANKL-mediated neddylation pathway thereby preventing or diminishing abnormal bone resorption and bone mass loss. According to another embodiment of the present disclosure, the effective amount of neddylation inhibitor on inhibiting the differentiation and/or function of osteoclasts does not affect the survival of osteoblast and osteogenesis process.

As would be appreciated, the present method can be applied to the subject, alone or in combination with additional therapies that possess some beneficial effects to the subject in terms of prophylaxis and/or treatment of osteoporosis and/or abnormal bone resorption. Depending on the intended purpose, the present method can be applied to the subject before, during, or after the administration of the additional therapies.

Optionally, the neddylation inhibitor may be administered to the subject via any of the following routes, which include, but are not limited to, oral, enteral, nasal, topical, transmucosal, and parenteral administration, in which the parenteral administration is any of subcutaneous, intradermal, intramuscular, intraarterial, intravenous, intraspinal, intrathecal or intraperitoneal injection.

The subject treatable by the present method is a mammal, for example, human, mouse, rat, guinea pig, hamster, monkey, swine, dog, cat, horse, sheep, goat, cow, and rabbit. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
Reagents
MLN4924 was obtained from Active Biochem (Activebiochem, Maplewood, N.J.). Recombinant mouse RANKL (GFM4) and recombinant mouse M-CSF (416-ML) were respectively obtained from Cell Guidance Systems LLC (Carlsbad, Calif.) and R&D (R&D, Minneapolis, Minn.). NFATc1 (7A6), APPBP1 (sc 360048), UBA3 (sc 377272) antibodies were obtained from Santa Cruz Biotechnology (Santa Cruz, Santa Cruz, Calif.). pERK (4370), pJNK (4668), pP38-MAPK (4631), and NEDD8 (2745) antibodies were purchased from Cell Signaling technology (CST, Beverly, Mass.). GAPDH, β-actin, and α-tubulin antibodies was purchased from GeneTex (GeneTex, Irvine, Calif.).

Cell Culture and Preparation of Primary Osteoclasts

RAW264.7 cells (murine monocytic/macrophage cell line) were cultured in Dulbecco's modified Eagle's medium high glucose (DMEM)(Gibco BRL, Gaithersburg, Md.) containing 10% fetal bovine serum (Gibco) and 1× GlutaMax (Gibco).

The pre-osteoclast cells were prepared by mouse bone marrow-derived macrophage (BMM). In brief, the femurs and tibias were obtained from 6-12 week old C57BL/6J female mice. The BMM cells were isolated from the femurs and tibias, and then cultured with M-CSF (40 ng/ml) for 3 days so as to produce the pre-osteoclasts of the monocyte/macrophage lineage.

All the cells were cultured in a 37° C. incubator containing 5% $CO_2$ and humidified air.

Osteoclast Formation

For in vitro osteoclast formation, the pre-osteoclasts and RAW264.7 cells were cultured in the medium containing 50 ng/ml sRANKL or specified concentrations of MLN4924 for seven days. Subsequently, the cells were fixed and stained for tartrate-resistant acid phosphatase (TRAP) by use of TRAP staining Kit (KAMIYA Biomedical Company, Seattle, Wash.) according to the manufacturer's protocol. The photos were visualized and snapped with Nikon TE300 microscope system (Nikon Instruments Inc., Melville, N.Y.).

Cathepsin K Activity Assay and Pit Assay

The pre-osteoclasts and RAW264.7 cells were seeded into Corning Osteo Surface Assay 96-wells plate (Corning, Kennebunk, Me.). Twenty-four hours later, the cells were treated with sRANKL (50 ng/ml) and specified concentrations of MLN4924 for 7 days. The cells were then harvested so as to evaluate the cathepsin K activity by use of Biovision Cathepsin K Activity Fluorometric Assay Kit (Biovision, Milpitas, Calif.). The Corning Osteo surface was stained with 1% toluidine blue for 24 hours and washed with deionized water twice. The photos of pit were snapped with Nikon TE300 microscope system at a magnification of 100× (Nikon, Melville, N.Y.).

Western Bolt Analysis

The RAW264.7 cells were starved with serum-free medium for six hours and then treated with the specified treatments. At indicated time points, the cells were washed with cold phosphate-buffered saline (PBS) and lysed in RIPA buffer containing complete protease inhibitor cocktail (Roche). The cell lysates were separated by SDS-PAGE followed by Western blotting with the indicated antibodies, including NEDD8, APPBP1, UBA3.

UBA3 Knockdown on Osteoclast Differentiation

RAW264.7 cells were seed on wells and were transfected with three specific UBA3 or scrambled siRNAs (GenePharma), including UBA3 siRNA 1 (Uba3-MUS-110), UBA3 siRNA 2 (Uba3-MUS-574), UBA3 siRNA 3 (Uba3-MUS-627) and scrambled siRNA (as the negative control), the nucleotide sequences thereof were summarized in Table 1.

TABLE 1

Nucleotide sequences of siRNA for inhibiting UBA3 expression

| Name | Nucleotide sequence | SEQ ID NO |
|---|---|---|
| UBA3 siRNA 1-sense | 5'-GGAGCCAAUGG CUGUUGAUU-3' | 1 |
| UBA3 siRNA 1-anti-sense | 5'-TTCCUCGGUUA CCGACAACUA-3' | 2 |
| UBA3 siRNA 2-sense | 5'-GGAUCAAUGGA AUGCUGAUU-3' | 3 |
| UBA3 siRNA 2-anti-sense | 5'-TTCCUAGUUAC CUUACGACUA-3' | 4 |
| UBA3 siRNA 3-sense | 5'-CCAAGCUCCAU UGUACCUUU-3' | 5 |
| UBA3 siRNA 3-anti-sense | 5'-TTGGUUCGAGG UAACAUGGAA-3' | 6 |
| Scrambled siRNA-sense | 5'-UUCUCCGAACG UGUCACGUU-3' | 7 |
| Scrambled siRNA-anti-sense | 5'-TTAAGAGGCUU GCACAGUGCA-3' | 8 |

Six hours' post-transfection, the cells were treated with sRANKL (50 ng/ml). Three days later, the effect of UBA3 knockdown on mature giant osteoclast formation on wells was photographed and counted.

Animal Model

All experimental procedures were approved by the Institutional Animal Care and Use Committee of the Chang Gung Memorial Hospital at Chiayi and complied with the Guideline for the Care and Use of Laboratory Animals available through the National Academy of Sciences (IACUC number: 2013100102 and 2015103001). All efforts were made to minimize the suffering of the animals. C57BL/6J female mice (6-8 weeks old; obtained from BioLasco in Taiwan) were operated ovariectomy surgery (OVX). 48 hours later of OVX operation, sRANKL (1 mg/kg) or saline was injected intraperitoneally once daily for two days followed by intraperitoneal injection of MLN4924 (10 mg/kg) once daily for 2 weeks. Mice were sacrificed with $CO_2$ asphyxiation, and the tibias and femurs were isolated therefrom. The tibias were subject to histochemistry assay, and the femurs were subject to bending test and tomographic analysis by MTS (Testresources, Shakopee, Minn.) and Skyscan 1272 (Bruker, Kontich, Belgium), respectively. Serum levels of cross linked C-telopeptide of type I collagen (CTX-1) (CEA665Mu) was measured by specific ELISA kit (USCN life science incorporation, Wuhan, Hubei, China).

Biomechanical Testing

The femurs were tested to failure by three-point bending on an MTS Synergie 200 (Testresources, Shakopee, Minn.). The speed of load application was set as 1 mm/min with preload of 1N, load cell of 500N, settling time of 30 seconds and distance between the points of 10 mm. Force-displacement data were plotted from the structural properties, including modulus, load at break, stress at yield and strain at yield.

Statistical Analysis

Data are presented as the mean±standard deviation (mean±SD). The significance of the difference between groups was evaluated with the unpaired Student t test, and a P value of 0.05 was considered significant.

Example 1 MLN4924 Inhibits the Differentiation of Osteoclasts

The effect of MLN4924 on the BMM or RAW264.7 cells was investigated in this example. Results are respectively depicted in FIGS. 1-2.

1.1 BMM

The primary BMMs isolated from mouse tibias and femurs were cultured in the medium containing M-CSF, sRANKL and specified concentrations of MLN4924 followed by TRAP staining. In general, the large multinucleated red TRAP-positive cells represented the mature osteoclasts. FIG. 1A are photographs of TRAP staining depicting the differentiation of osteoclasts from BMMs. Compared to the control group, sRANKL notably stimulated the osteoclast differentiation of BMMs. Furthermore, MLN4924 obviously suppressed the sRANKL-mediated osteoclast formation in a dose-dependent manner.

The effect of MLN4924 on the activity of osteoclast was then confirmed by pit assay. Similarly, the primary BMMs were cultured in the medium containing specified dose of M-CSF, sRANKL, and MLN4924 for 7 days. The resorbing areas on bone matrix by osteoclasts were visualized by 1% toluidine blue staining and quantified by image software. As the data of FIG. 1B indicated, MLN4924 suppressed the resorbing activity of osteoclasts in a dose-dependent manner.

It is known that osteoclasts secrete cathepsin K to degrade collagen and other matrix proteins during bone resorption. Accordingly, the present invention further investigated the effect of MLN4924 on the activity/function of cathepsin K. It is found that, sRANKL notably up-regulated the activity of cathepsin K; whereas compared to the sRANKL group, treatment with MLN4924 significantly reduced the activity of cathepsin K. Moreover, treatment with MLN4924 along did not affect the basal activity of cathepsin K in macrophages (FIG. 1C).

Figure 1B:
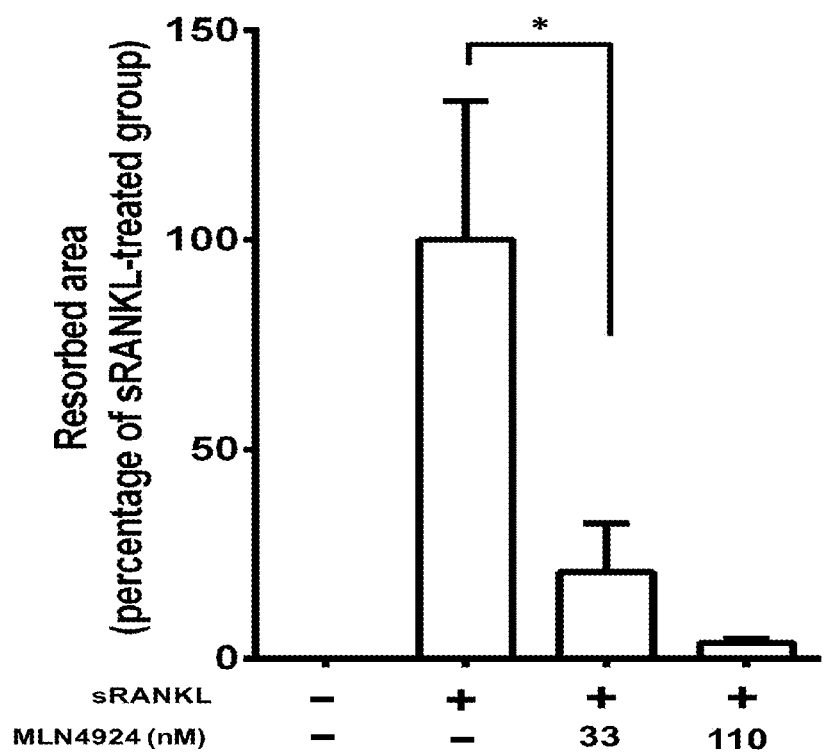
Figure 1C:
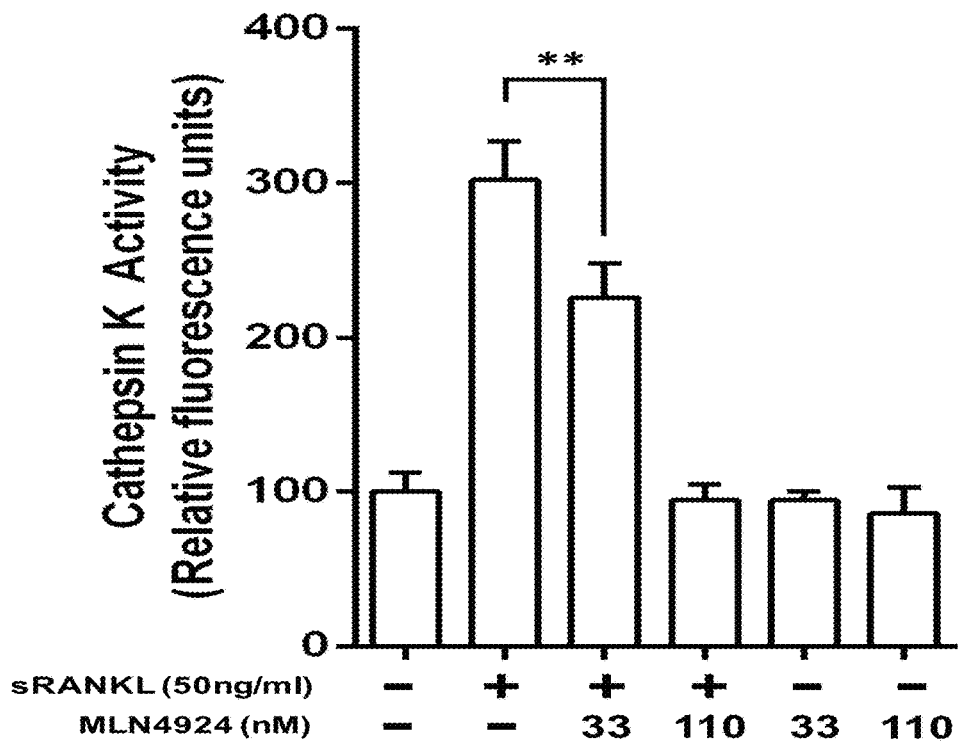

FIGS. 1B and 1C indicate that MLN4924 can diminish abnormal bone resorption via suppressing the differentiation and bone resorbing activity of osteoclasts.

Figure 1D:
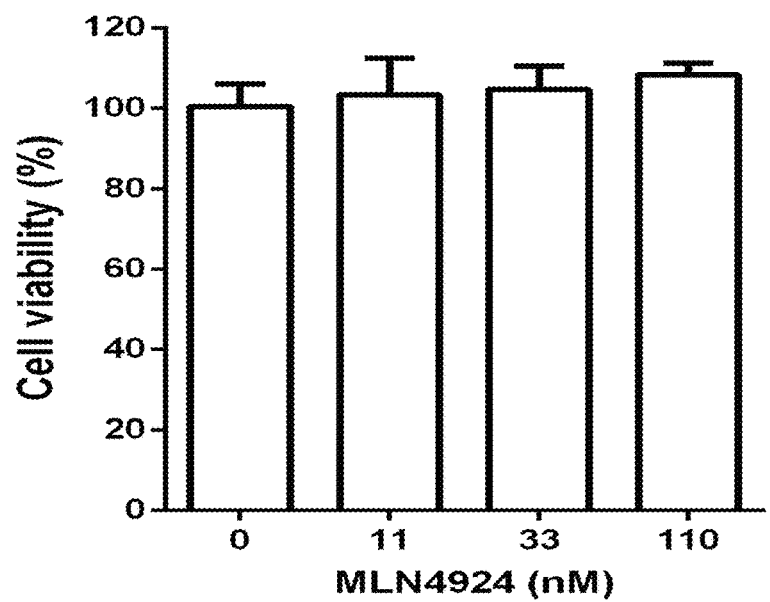

Next, the WST assay was used to determine whether the suppressed osteoclastogenesis by MLN4924 was caused by cytotoxicity. The data indicated that MLN4924 had no cytotoxic effects at doses that effectively inhibited osteoclast differentiation (FIG. 1D).

1.2 RAW264.7

Figure 2A:
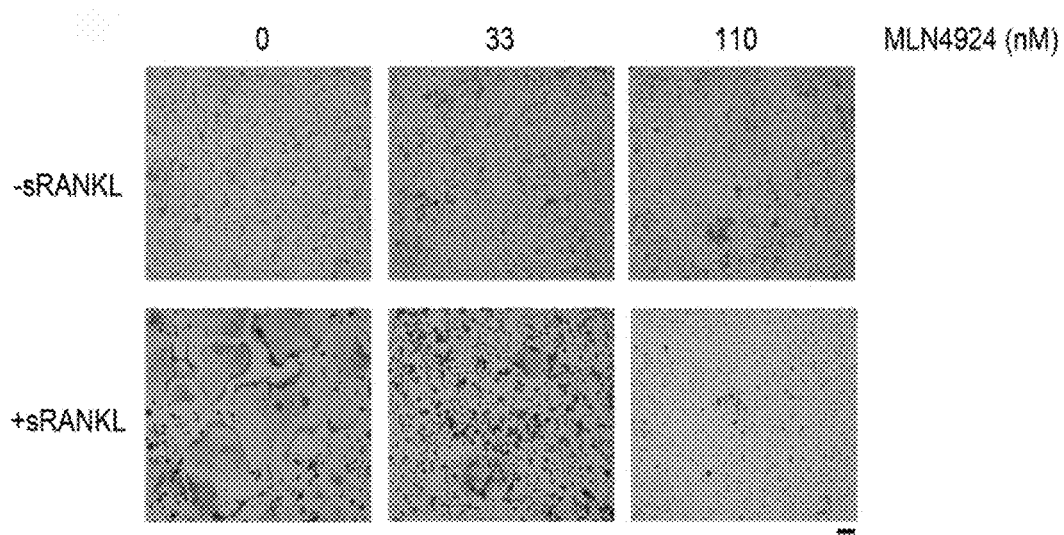
FIGS. 2A-2D are data collected from RAW264.7 cells respectively incubated in the medium containing sRANKL (50 ng/ml) and specified concentrations of MLN4924 for 7 days according to example 1.2 of the present disclosure.
Figure 2B:
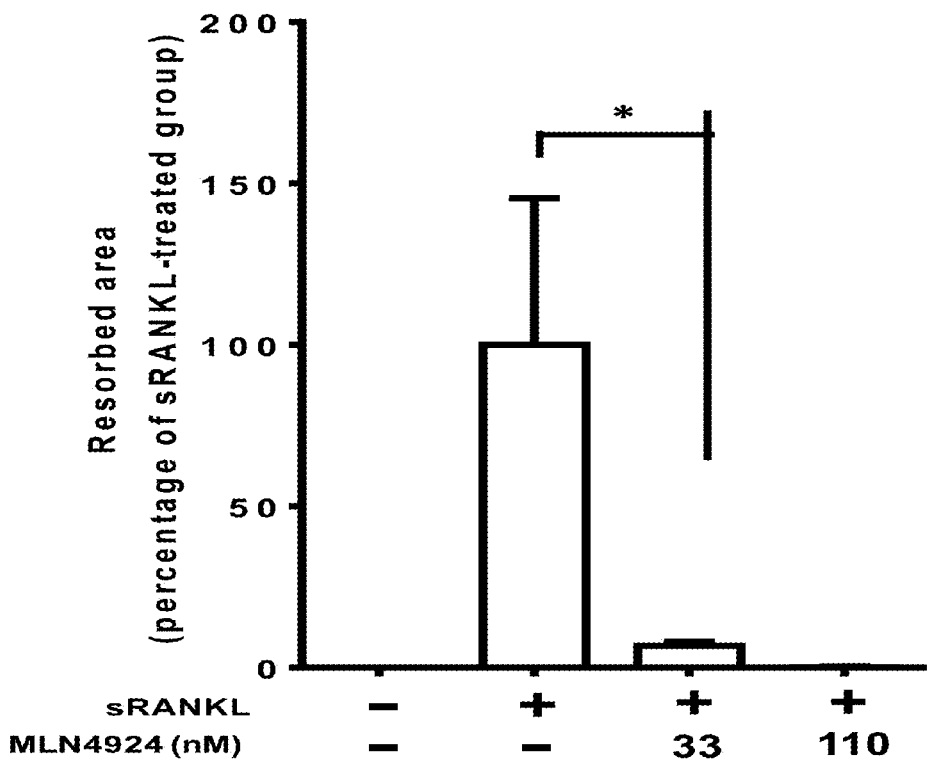
Figure 2C:
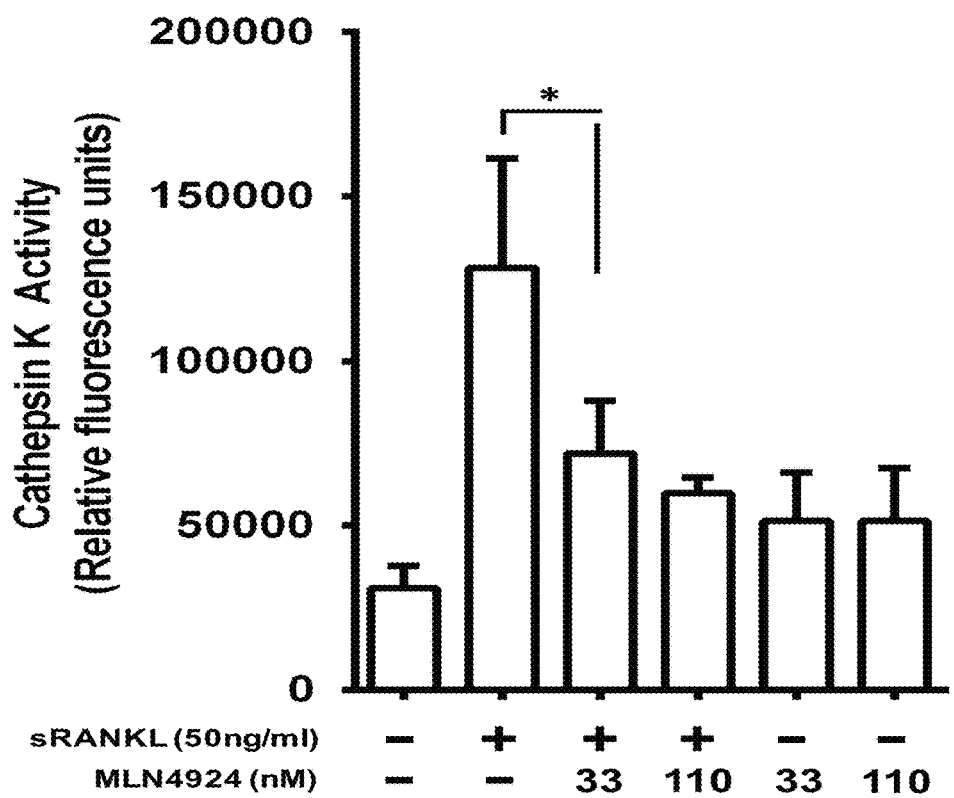
Figure 2D:
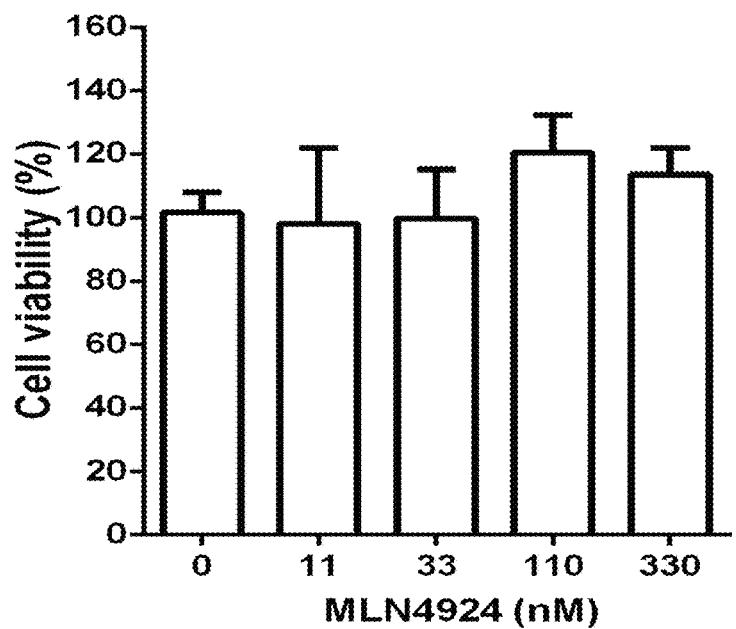

In addition to BMMs, the effect of MLN4924 on macrophage cell line RAW264.7 cells was also investigated. The RAW264.7 cells were cultured in the medium containing sRANKL and MLN4924 for 7 days, then subjected to osteoclast formation evaluation by TRAP staining. It was found that MLN4924 significantly inhibited the differentiation (FIG. 2A), bone matrix resorption (FIG. 2B) and osteolytic enzyme cathepsin K activity (FIG. 2C) of osteoclasts derived from sRANKL-activated RAW264.7 cells. Further, MLN4924 did not affect cell viability of the RAW264.7 cells, indicating that MLN4924 had no cytotoxic effect at doses that effectively inhibited osteoclast differentiation (FIG. 2D).

These data of FIGS. 2A-2D confirmed that without affecting the viability of macrophages, MLN4924 can significantly suppress the differentiation and osteolytic activity of osteoclasts for preventing bone resorption.

Example 2 Inhibitory Mechanism

Figure 3A:
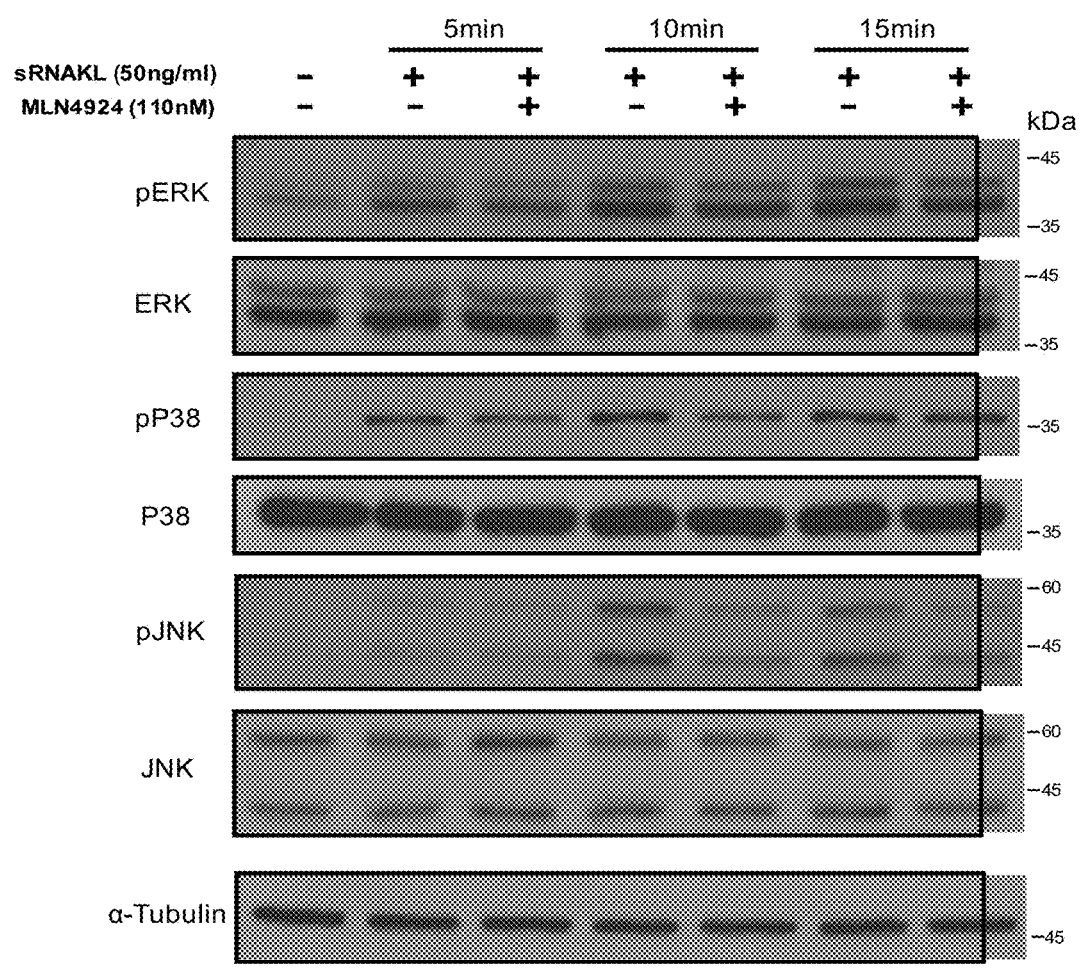
FIGS. 3A-3D are data collected from Western blot analysis that respectively depict the expression of specified protein extracted from the RAW264.7 cells, which are pretreated with specified concentrations of MLN4924 for 30 minutes followed by the stimulation of sRANKL (50 ng/ml) according to example 2 of the present disclosure.
Figure 3B:
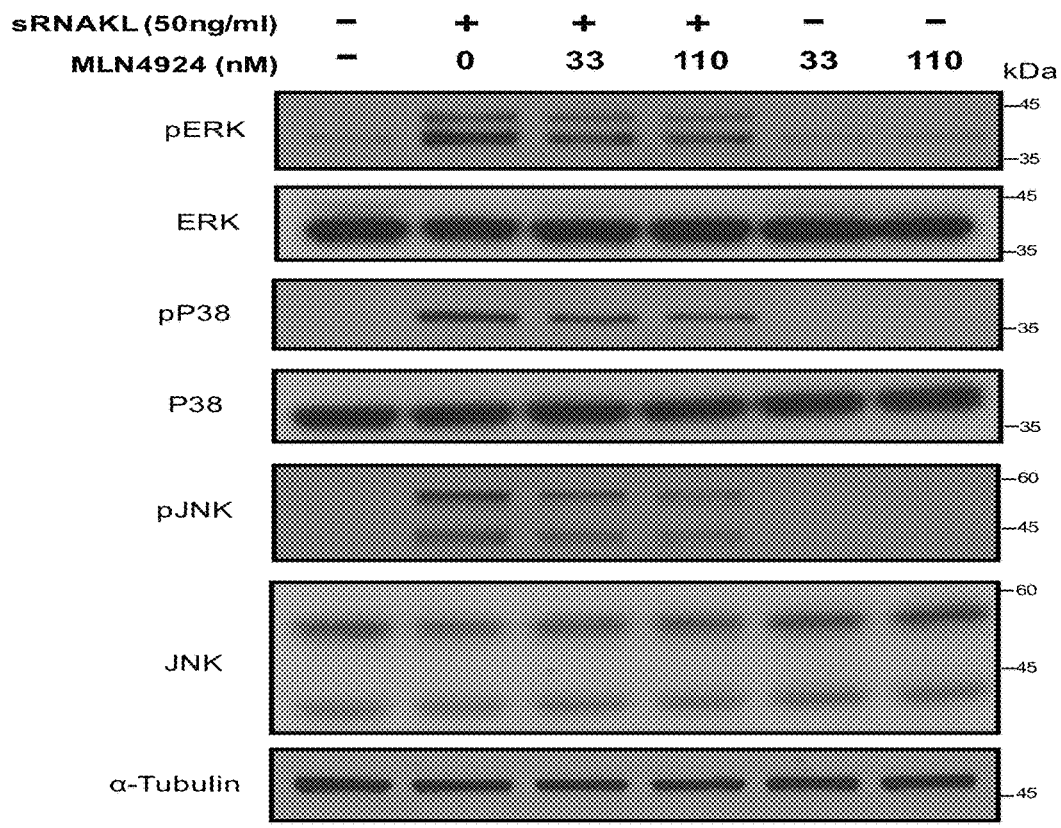

The data of Western blot analysis revealed the time and dose effect of MLN4924 on sRANKL-activated osteoclast differentiating signals. The result showed that compared with the vehicle control (Mock), sRANKL obviously increased the phosphorylations of ERK (pERK), P38 (pP38) and JNK (pJNK) (FIG. 3A). The sRANKL-upregulated phosphorylations of ERK (pERK), P38 (pP38), and JNK (pJNK) were inhibited by the treatment of MLN4924 (FIG. 3A). Specifically, the inhibitory effect increased with an increase in the MLN4924 concentration (FIG. 3B).

Figure 3C:
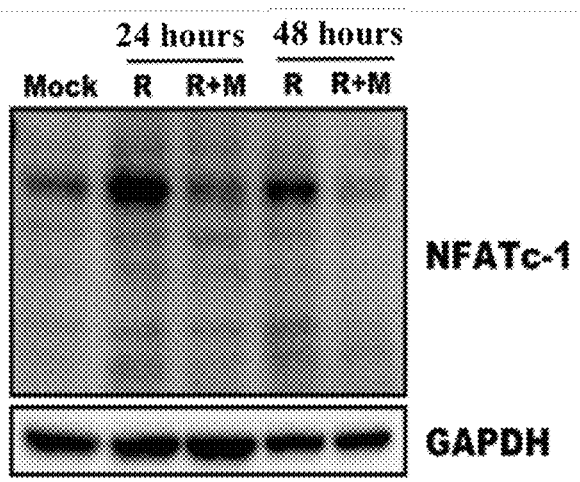
Figure 3D:
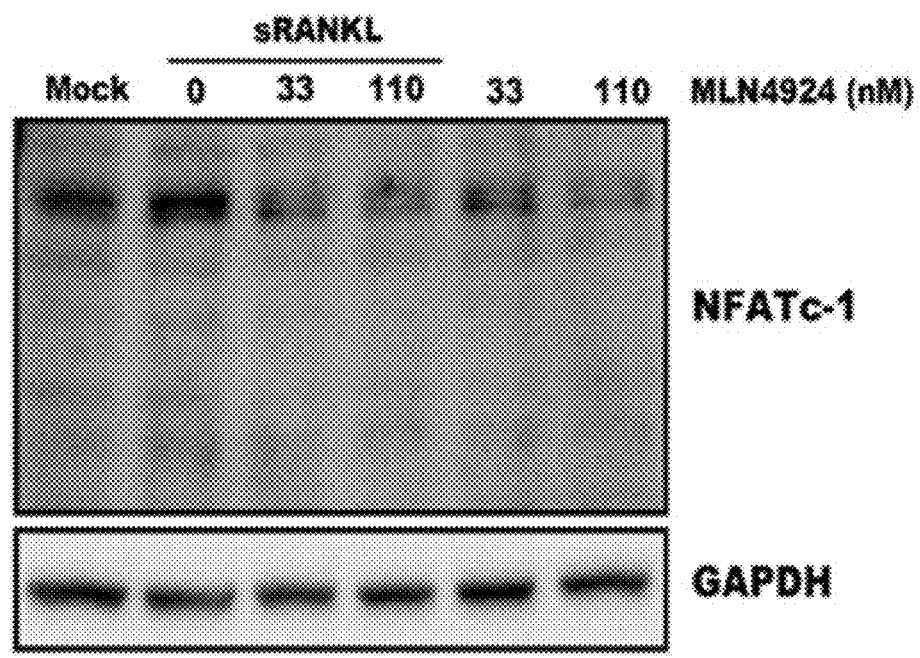

Previous studies have reported that RANKL induced the expression of transcription factor NFATc-1, and the stem cell isolated from the NFATc-1-deficient embryo failed to differentiate to osteoclasts. In addition, ectopic expression of NFATc-1 in the pre-osteoclasts rendered the pre-osteoclast differentiated to osteoclasts in the absence of RANKL. Since NFATc-1 is considered as a key transcription factor for osteoclast differentiation, the effect of MLN4924 on the level of NFATc-1 was thus investigated. As the data of FIG. 3C illustrated, sRANKL increased the expression of NFATc-1 ("R" group), and the expression of NFATc-1 induced by sRANKL was significant suppressed by MLN4924 ("R+M" group). The data of FIG. 3D confirmed that the inhibitory effect of MLN4924 on the NFATc-1 expression increased with an increase in the MLN4924 concentration.

The above-mentioned data indicated that MLN4924 inhibited the differentiation and activity of osteoclasts via down-regulating RANKL signaling pathway in a time- and dose-dependent manner.

Example 3 Effect of MLN4924 on Osteoblasts

Figure 4A:
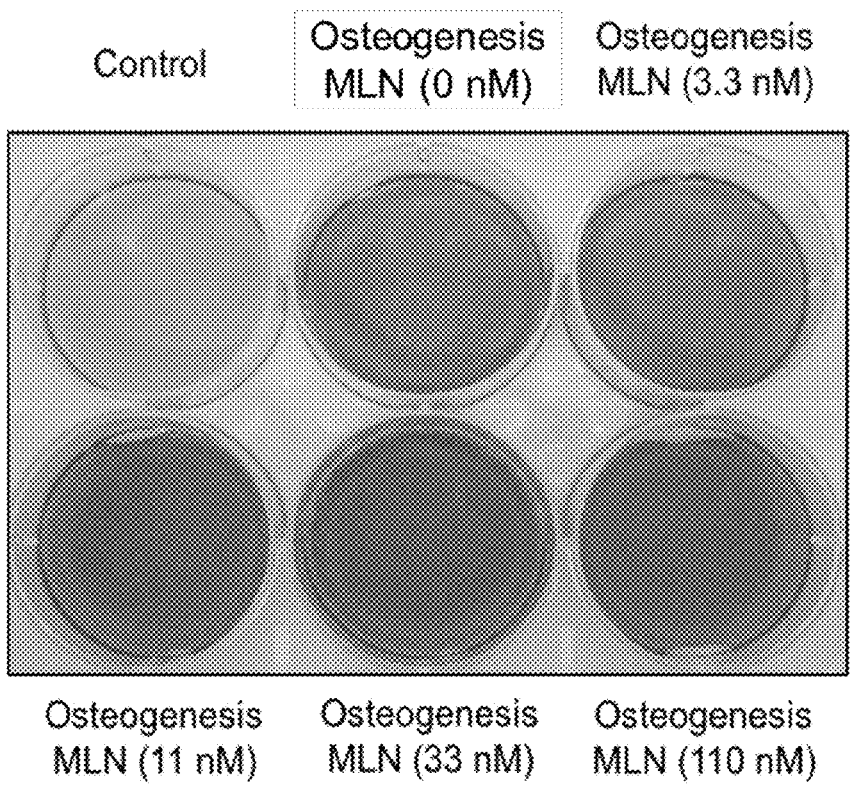
FIGS. 4A-4B respectively depict the osteogenesis of mouse pre-osteoblast cell line MC3T3-E1 cells incubated in the differentiation medium containing specified concentrations of MLN4924 for 21 days according to example 3 of the present disclosure.
Figure 4B:
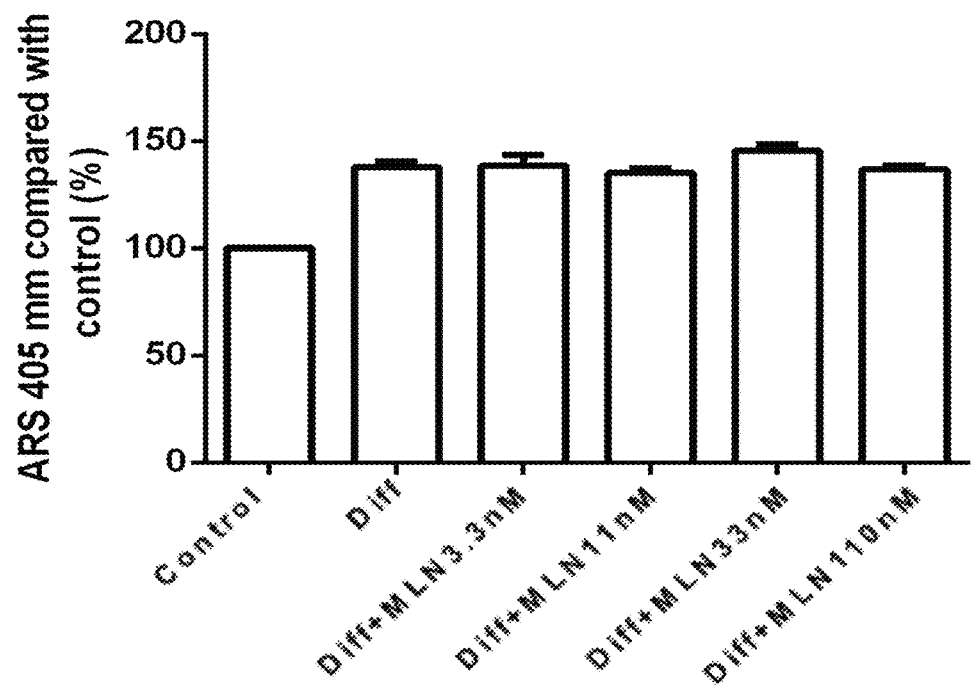

Next, whether treatment with MLN4924 would affect (i.e., increase or decrease) osteoblasts and the osteogenesis process were investigated. Results were respectively illustrated in FIGS. 4A-4B.

The mouse pre-osteoblast cell line MC3T3-E1 cells were cultured in osteoblast differentiation medium with or without MLN4924 for 21 days. It was found that neither the survival of osteoblasts (FIG. 4A), nor the differentiation of osteoblasts (FIG. 4B) was affected by MLN4924.

The data indicated that MLN4924 had no cytotoxic effect on the survival and differentiation of osteoblasts at doses that effectively inhibited osteoclast differentiation.

Example 4 siRNA Specific for UBA3 Inhibits the Differentiation of Osteoclasts

RANK is a member of the tumor necrosis factor receptor family expressed by osteoclasts and their precursors. The interaction of RANK with its soluble ligand (i.e., sRANKL) has been identified as the critical pathway to control bone resorption. However, the function of neddylation pathway on regulating sRANKL-activated osteoclast differentiation is mostly unknown. In order to investigate the importance and therapeutic significance of neddylation pathway in osteoporosis, the expression pattern of neddylation pathway and the knockdown of UBA3, which decreases NAE-mediated neddylation activity, on affecting sRANKL-stimulated osteoclastic differentiation was examined.

Figure 5A:
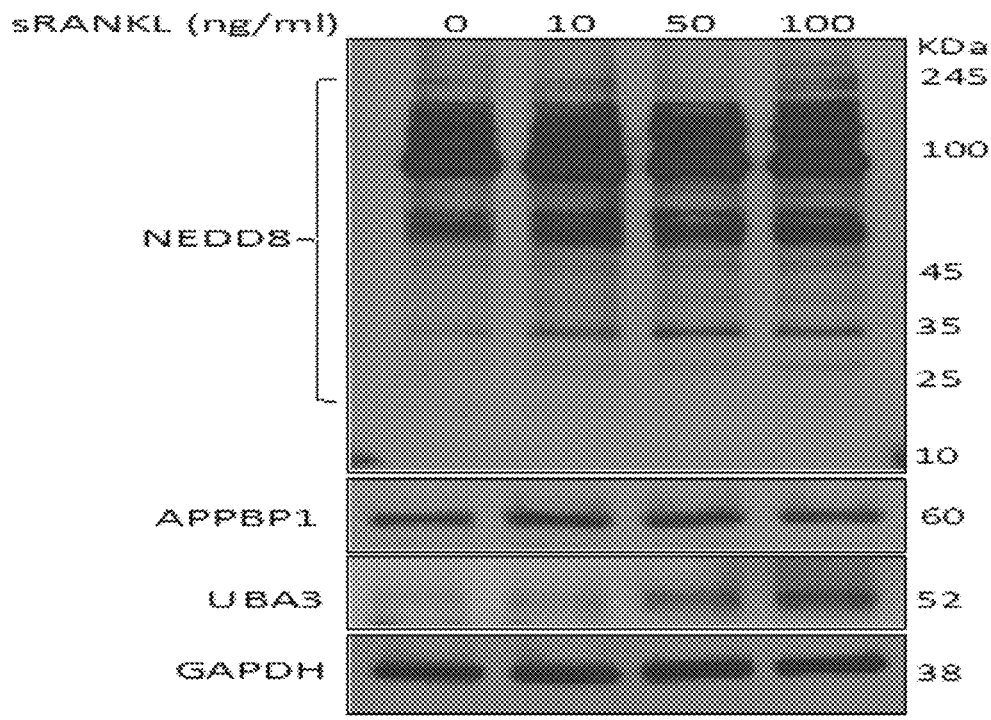
FIGS. 5A-5D are the data respectively depicting the effect of sRANKL on the neddylation pathway and the knockdown effect of UBA3 siRNA on macrophages during osteoclast differentiation according to example 4 of the present disclosure.

The dose effect of sRANKL on stimulating neddylation pathway activation and differentiation of osteoclasts and was performed. FIG. 5A showed that that sRANKL dose-dependently enhanced NEDD8 modification on proteins after 3-day incubation. Furthermore, the initiator of enzyme (E1) in neddylation is NAE which is a heterodimer composed of APPBP1 and UBA3 subunits. The data showed that sRANKL significantly increased the expression of catalytic subunit UBA3 but not regulatory subunit APPBP1 during sRANKL stimulation, indicating an important involvement of UBA3 subunit of NAE in sRANKL-mediated osteoclastic differentiation.

Figure 5B:
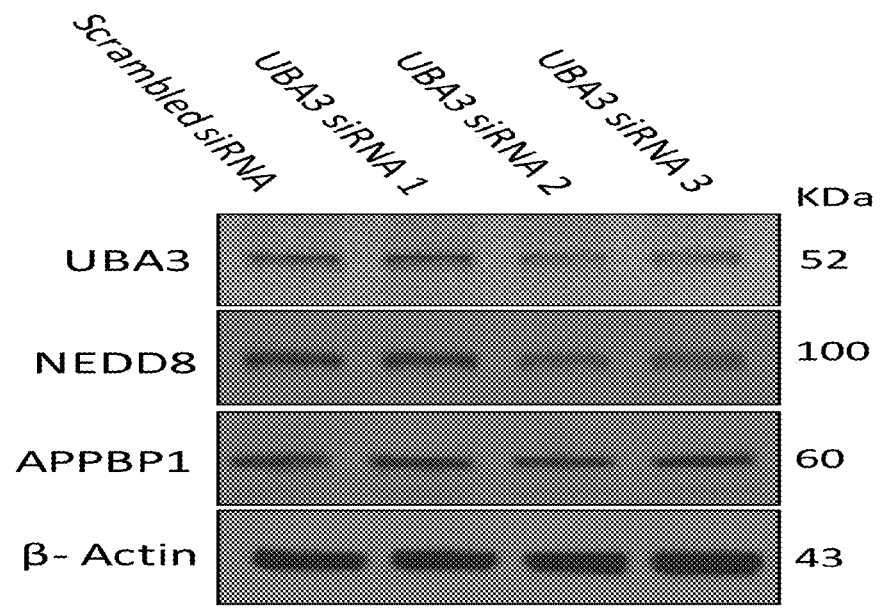
Figure 5C:
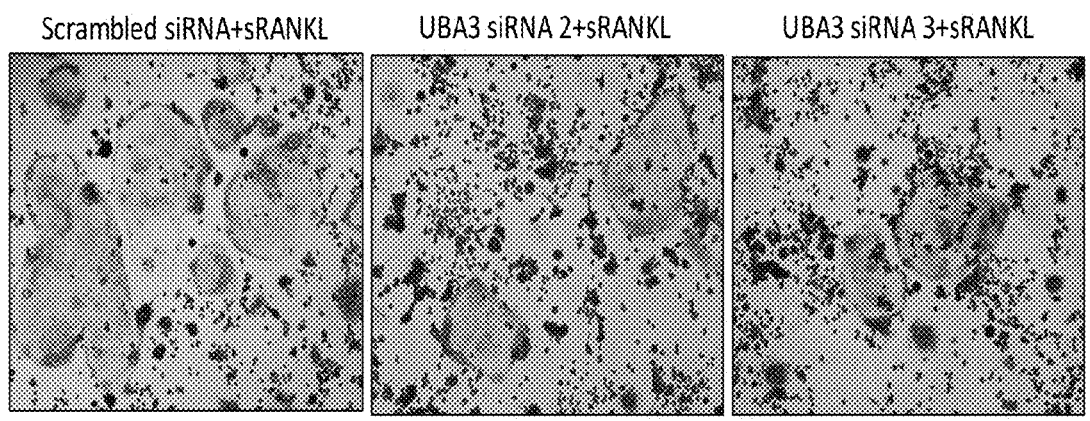
Figure 5D:
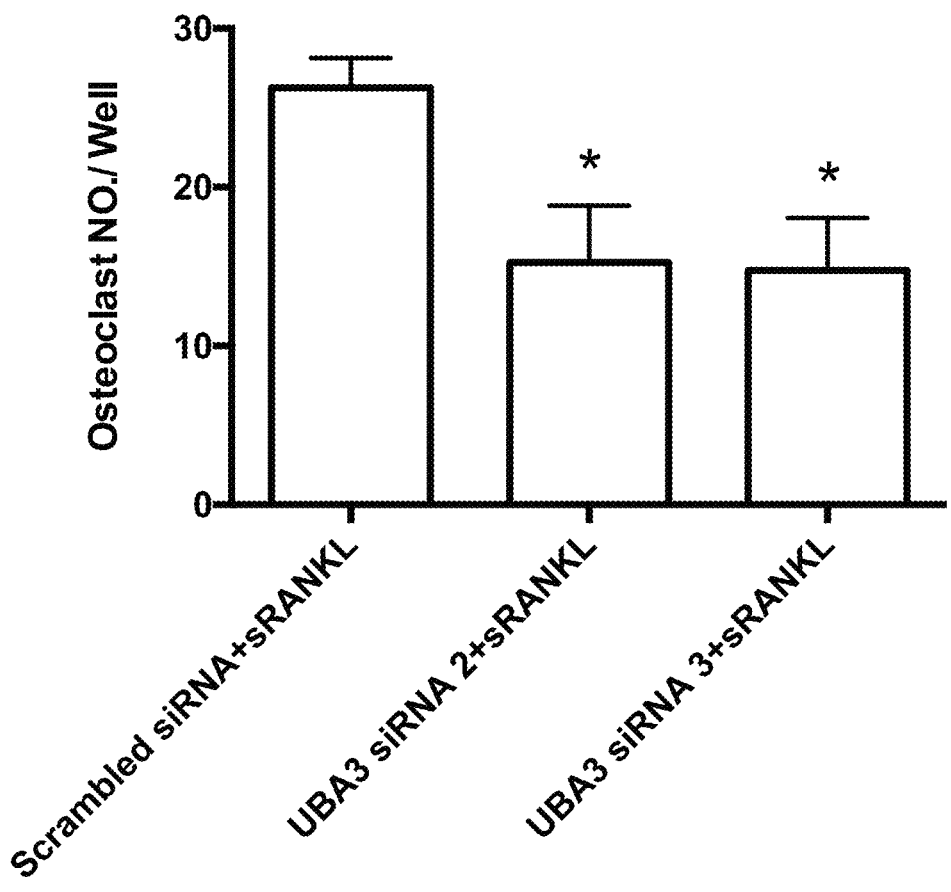

In order to determine the functional effect of UBA3 in sRANKL-activated osteoclastic differentiation, three specific RNAi molecules by targeting UBA3 mRNA were transfected into RAW264.7 for knockdowning UBA3 expression. After culture, the transfected RAW264.7 cells were harvested for checking UBA3 expression and were further treated with sRANKL for induction of osteoclastic differentiation. By Western blotting analysis, FIG. 5B showed that UBA3 siRNAs 2 and 3, but not UBA3 siRNA 1 and the scrambled control siRNA, can knockdown the expression of UBA3. Furthermore, knockdown of the UBA3 expression was followed with down-regulating NEDD8 modification but not affecting the expression of APPBP1. FIGS. 5C and 5D showed that the scrambled control siRNA had no effect on inhibiting sRANKL-stimulated osteoclastic differentiation. Whereas, both UBA3 siRNAs 2 and 3 significantly diminished the differentiating number of giant osteoclasts. These data indicate that the expression and activity of UBA3 is important in NAE-mediated protein neddylation during sRANKL-stimulated osteoclastic differentiation.

The data of FIGS. 5A-5D demonstrated that the siRNA specific for UBA3 exhibits an inhibitory effect on the differentiation of osteoclasts.

Example 5 In Vivo Effect of MLN4924

5.1 Bone Loss

The osteoporosis mouse model was used in this example to investigate whether MLN4924 can inhibit the differentiation and osteolytic function of osteoclasts via reducing abnormal bone resorption for curing the osteoporosis in vivo.

Figure 6A:
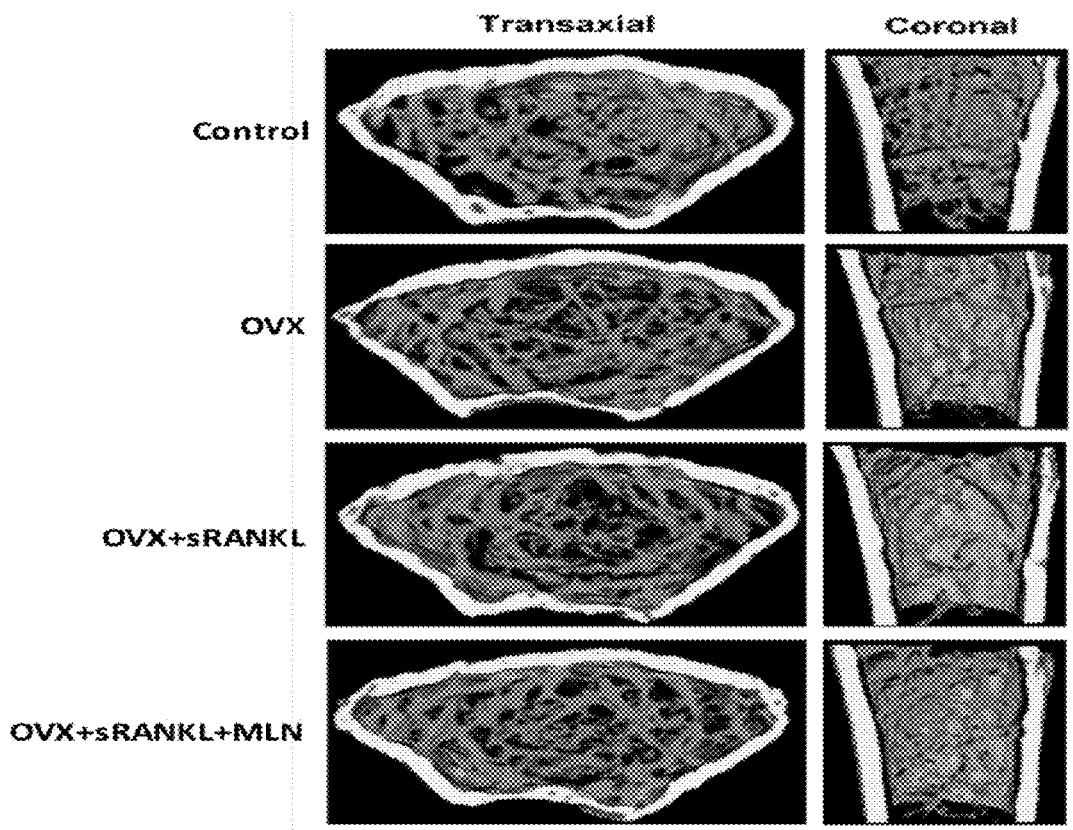
FIGS. 6A-6E are the data depicting the mouse model of ovariectomy-induced osteoporosis, in which the ovariectomized (OVX) mice are respectively treated with sRANKL (1 mg/Kg) in the absence or presence of MLN4924 (10 mg/Kg) according to example 5.1 of the present disclosure.

The mice were first treated with specified treatments before subjecting to micro-computed tomography (μCT). Compared with the control group, severe trabecular bone losses at distal femoral metaphysis were respectively found in the OVX group and OVX+sRANKL group; whereas the treatment of MLN4924 (OVX+sRANKL+MLN) group could rescue the trabecular bone loss caused by OVX+sRANKL treatment (FIG. 6A).

Figure 6B:
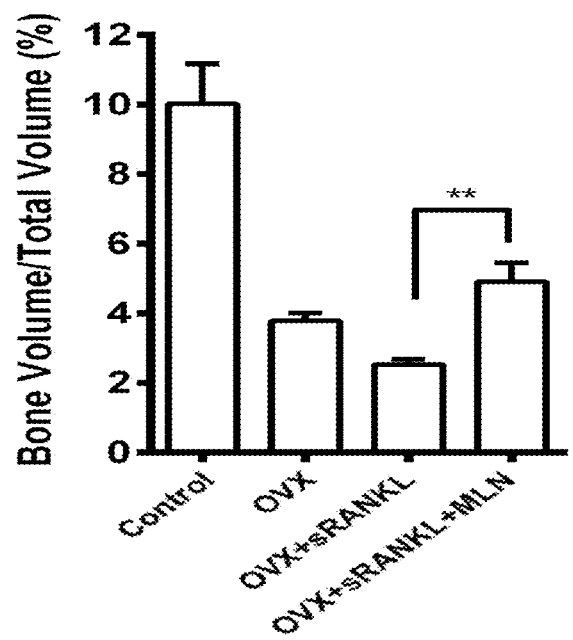
Figure 6C:
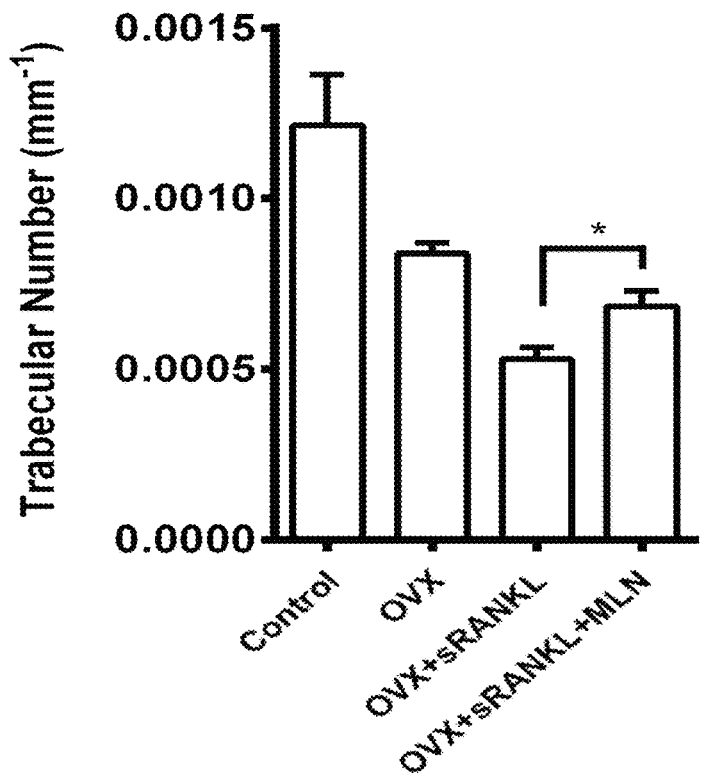
Figure 6D:
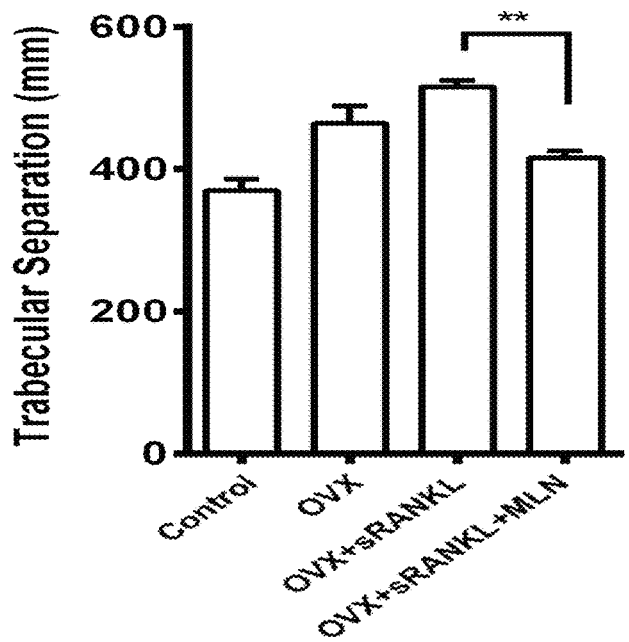

The effect of MLN4924 on trabecular bone parameters, including the bone volume/total tissue volume, trabecular number, and trabecular space in bone loss mice were then investigated, and results are presented in FIGS. 6B to 6D. Similar to the findings in FIG. 6A, MLN4924 significantly rescued the sRANKL-mediated trabecular bone loss in OVX mice as compared with the OVX+sRANKL group.

Figure 6E:
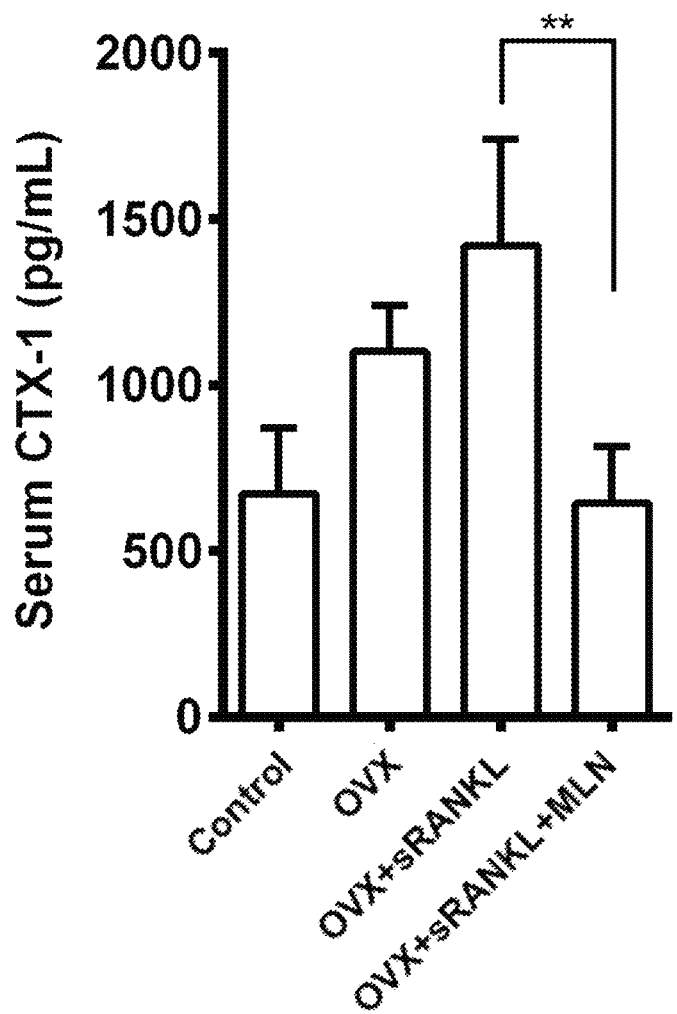
Figure 7A:
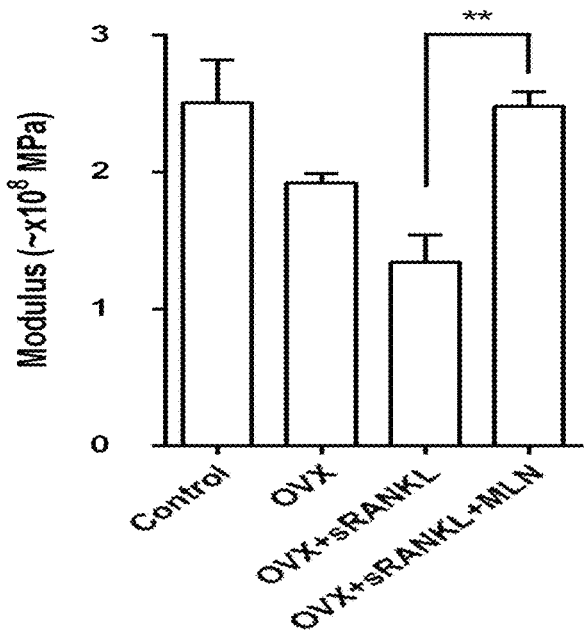
FIGS. 7A-7D are histograms respectively depicting the mechanical properties of femurs in control, OVX, OVX+RANKL, and OVX+RANKL+MLN4924 groups according to example 5.2 of the present disclosure, including modulus (FIG. 7A), strain at break (FIG. 7B), stress at yield (FIG. 7C), and load at break (FIG. 7D). Values are expressed as mean±SD, N=6 per group. *$p<0.05$; **$p<0.01$.
Figure 7B:
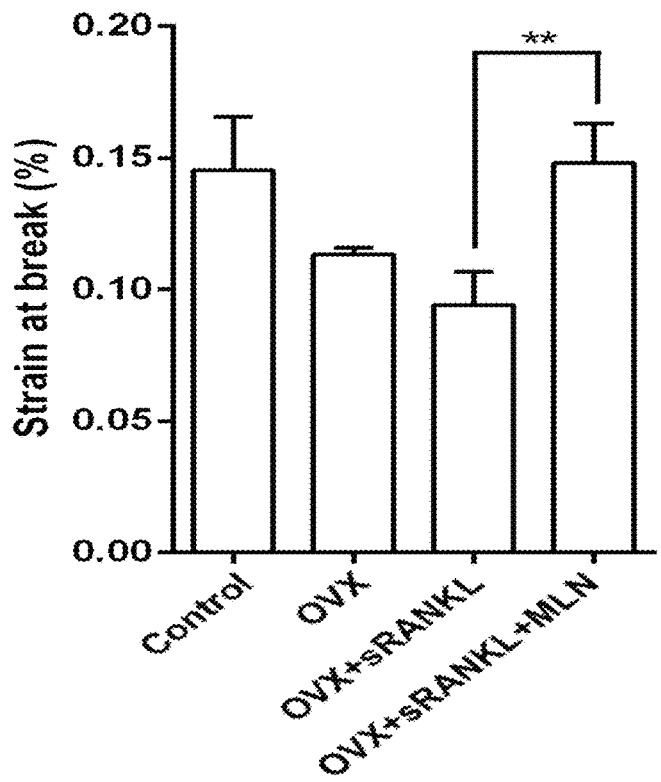
Figure 7C:
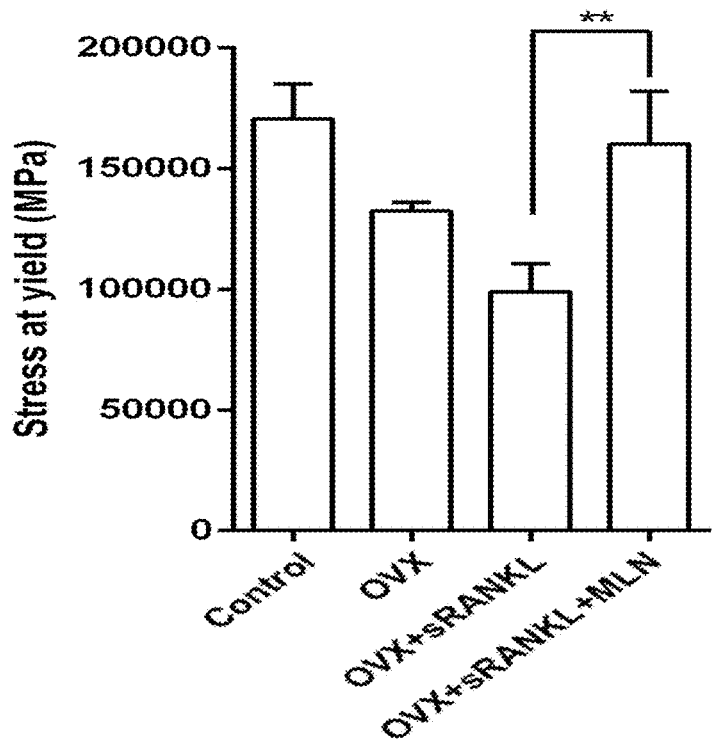
Figure 7D:
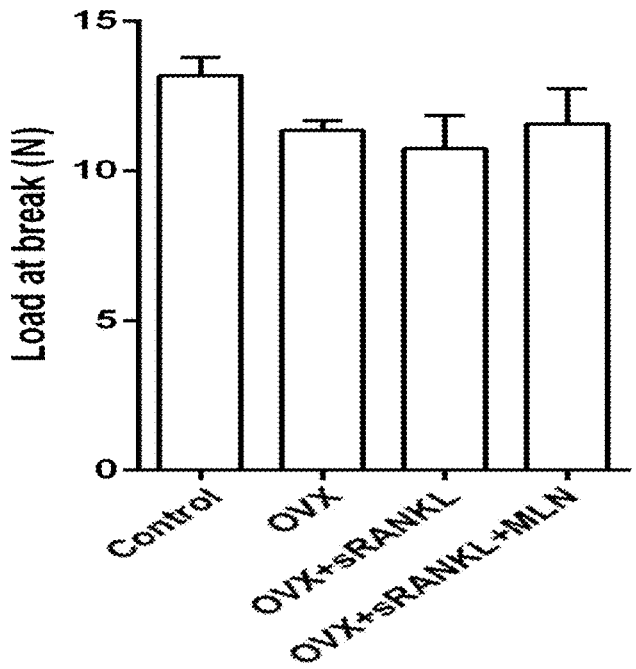

Since CTX-1 serve as the biomarker for bone resorption, the level of CTX-1 in the serum of mice receiving specified treatments were then determined. The result of ELISA analysis indicated that both the OVX and OVX+sRANKL treatments increased the serum CTX-1 level, while administration of MLN4924 significantly rescued the OVX+sRANKL-stimulated serum CTX-1 level upregulation (FIG. 6E).

The data in this example demonstrated that MLN4924 can significantly inhibit abnormal bone resorption for preventing bone loss in osteoporosis in vivo.

5.2 Biomechanical Property

Bone loss results in bone fragile, thus rendering bone being easier to break. In this example, mice were first treated with OVX or OVX+sRANKL to cause bone loss, and then MLN4924 was administered. The femurs of mice were then subject to shaft fracture testing by three-point bending so as to evaluate the biomechanical properties thereof.

The data of FIGS. 7A-7D indicated that compared with the control group, levels of relevant bone loss parameters such as modulus (FIG. 7A), strain at break (FIG. 7B), stress at yield (FIG. 7C), and load at break (FIG. 7D) were significantly reduced in OVX and OVX+sRANKL groups; while MLN4924 treatment prevented the levels of these parameters from dropping. Thee data indicated that MLN4924 can significantly suppress abnormal bone loss for preventing bone strength reduction in osteoporosis in vivo.

In conclusion, inventors of the present disclosure had identified a novel use of neddylation inhibition by neddylation inhibitor (e.g., MLN4924 or UBA3 siRNA), which is useful in preventing and/or treating abnormal bone resorption and/or osteoporosis via inhibiting the formation and osteolytic function of osteoclasts. Accordingly, the present disclosure provides a method of preventing and/or treating abnormal bone resorption and/or osteoporosis, in which an effective amount of a neddylation inhibitor (e.g., MLN4924 or UBA3 siRNA) may be administered to a subject in need thereof so as to prevent the development of abnormal bone resorption and/or osteoporosis, and/or alleviate/ameliorate the symptoms associated with abnormal bone resorption and/or osteoporosis.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of preventing and/or treating osteoporosis in a subject in need thereof, comprising administering to the subject an effective amount of an NEDD8-activating enzyme (NAE) inhibitor.

2. The method of claim 1, wherein the NAE inhibitor is
   a compound selected from the group consisting of, MLN4924 and the analog and derivative thereof, TAS4464, 6,6"-biapigenin, cyclometallated rhodium (III) complex, and flavokawain A; or
   a nucleic acid comprising the sequence of SEQ ID NO: 4 or 6, or a DNA sequence corresponding thereto.

3. The method of claim 2, wherein the compound is MLN4924.

4. The method of claim 2, wherein the nucleic acid is a small interference ribonucleic acid (siRNA), a small hairpin ribonucleic acid (shRNA), or a micro-ribonucleic acids (miRNA).

5. The method of claim 1, wherein the subject is a human, and the effective amount is about 0.01-100 mg/kg body weigh per day.

6. The method of claim 5, wherein the effective amount is about 0.1-10 mg/kg body weigh per day.

7. The method of claim 6, wherein the effective amount is about 0.1-2 mg/kg body weigh per day.

8. The method of claim 5, wherein the NAE inhibitor is administered to the subject daily for at least 7 consecutive days.

9. The method of claim 8, wherein the NAE inhibitor is administered to the subject daily for at least 14 consecutive days.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: synthesized

<400> SEQUENCE: 1
ggagccaaug gcuguugaut t                                           21

<210> SEQ ID NO 2
<211> LENGTH: 21
<212> TYPE: DNA
<213> ORGANISM: Artificial Sequence
<220> FEATURE:
<223> OTHER INFORMATION: synthesized

<400> SEQUENCE: 2
ttccucgguu accgacaacu a                                           21

<210> SEQ ID NO 3
<211> LENGTH: 21
<212> TYPE: DNA
<213> ORGANISM: Artificial Sequence
<220> FEATURE:
<223> OTHER INFORMATION: synthesized

<400> SEQUENCE: 3
ggaucaaugg aaugcugaut t                                           21

<210> SEQ ID NO 4
<211> LENGTH: 21
<212> TYPE: DNA
<213> ORGANISM: Artificial Sequence
<220> FEATURE:
<223> OTHER INFORMATION: synthesized

<400> SEQUENCE: 4
ttccuaguua ccuuacgacu a                                           21

<210> SEQ ID NO 5
<211> LENGTH: 21
<212> TYPE: DNA

```
<213> ORGANISM: Artificial Sequence
<220> FEATURE:
<223> OTHER INFORMATION: synthesized

<400> SEQUENCE: 5
ccaagcucca uuguaccuut t                                              21

<210> SEQ ID NO 6
<211> LENGTH: 21
<212> TYPE: DNA
<213> ORGANISM: Artificial Sequence
<220> FEATURE:
<223> OTHER INFORMATION: synthesized

<400> SEQUENCE: 6
ttgguucgag guaacaugga a                                              21

<210> SEQ ID NO 7
<211> LENGTH: 21
<212> TYPE: DNA
<213> ORGANISM: Artificial Sequence
<220> FEATURE:
<223> OTHER INFORMATION: synthesized

<400> SEQUENCE: 7
uucuccgaac gugucacgut t                                              21

<210> SEQ ID NO 8
<211> LENGTH: 21
<212> TYPE: DNA
<213> ORGANISM: Artificial Sequence
<220> FEATURE:
<223> OTHER INFORMATION: synthesized

<400> SEQUENCE: 8
ttaagaggcu ugcacagugc a                                              21
```